US011692270B2

(12) United States Patent
Vaidyanathan et al.

(10) Patent No.: US 11,692,270 B2
(45) Date of Patent: Jul. 4, 2023

(54) SYSTEM FOR SURFACE MODIFICATION BY LASER DIFFUSION

(71) Applicant: University of Central Florida Research Foundation, Inc., Orlando, FL (US)

(72) Inventors: Rajan Vaidyanathan, Oviedo, FL (US); Aravinda Kar, Oviedo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 180 days.

(21) Appl. No.: 16/431,519

(22) Filed: Jun. 4, 2019

(65) Prior Publication Data
US 2019/0284699 A1  Sep. 19, 2019

Related U.S. Application Data

(62) Division of application No. 13/969,055, filed on Aug. 16, 2013, now Pat. No. 10,358,723.
(Continued)

(51) Int. Cl.
*C23C 16/48* (2006.01)
*C23C 16/54* (2006.01)
(Continued)

(52) U.S. Cl.
CPC ............ *C23C 16/56* (2013.01); *A61L 27/306* (2013.01); *A61L 31/088* (2013.01); *C23C 10/28* (2013.01);
(Continued)

(58) Field of Classification Search
CPC ..... C23C 16/56; C23C 16/483; C23C 16/545; A61L 27/306; A61L 31/088; A61L 2420/02; A61L 2420/06; A61N 1/086
(Continued)

(56) References Cited

U.S. PATENT DOCUMENTS 5,156,697 A   10/1992  Bourell et al.
5,288,325 A *  2/1994  Gomi .................. C23C 16/4482
                                                    118/712
(Continued)

FOREIGN PATENT DOCUMENTS

WO   WO2006064059   6/2006

OTHER PUBLICATIONS

Brown et al. "Nanofibers and Nanotechnology in Textiles—6.5 Purification Techniques", 2007, Woodhead Publishing, p. 152-193.
*** See Priority Application U.S. Pat. No. 10,358,723.
(Continued)

*Primary Examiner* — Charlee J. C. Bennett
(74) *Attorney, Agent, or Firm* — Allen, Dyer, Doppelt + Gilchrist, PA

(57) ABSTRACT

A system for forming surface modified substrates includes a laser system, and a laser processing chamber. A laser scanner automatically controls a position of the laser beam or an x-y translating stage upon which the laser processing chamber is mounted thereon for scanning the laser beam relative to a substrate of material (M) having a bulk portion and an outer surface integrated with the bulk portion, and a coating including metal organic molecules including at least one metal X or particles of metal X on the outer surface. At laser-heated spots atoms of X from the metal coating diffuse into the outer surface to form a modified surface layer including both M and X. The modified surface layer has a thickness of 1 nm, and a 25° C. electrical conductivity ≥2.5% above or ≤2.5% below a 25° C. electrical conductivity in the bulk portion.

3 Claims, 4 Drawing Sheets

Related U.S. Application Data

(60) Provisional application No. 61/683,897, filed on Aug. 16, 2012.

(51) Int. Cl.

| | | |
|---|---|---|
| *C23C 16/56* | (2006.01) | |
| *A61L 27/30* | (2006.01) | |
| *A61L 31/08* | (2006.01) | |
| *C23C 10/28* | (2006.01) | |
| *A61N 1/08* | (2006.01) | |

(52) U.S. Cl.
CPC .......... *C23C 16/483* (2013.01); *C23C 16/545* (2013.01); *A61L 2420/02* (2013.01); *A61L 2420/06* (2013.01); *A61N 1/086* (2017.08)

(58) Field of Classification Search
USPC .......... 118/722, 715–733; 156/345.1–345.55
See application file for complete search history.

(56) References Cited

U.S. PATENT DOCUMENTS

| | | | |
|---|---|---|---|
| 6,943,964 B1 | 9/2005 | Zhang et al. | |
| 7,336,359 B1* | 2/2008 | Simpson | G01N 21/211 |
| | | | 356/369 |
| 8,409,909 B2 | 4/2013 | Nagaraja | |
| 2004/0140945 A1 | 7/2004 | Werner et al. | |
| 2005/0078048 A1 | 4/2005 | Delgado et al. | |
| 2005/0095866 A1* | 5/2005 | Toyoda | H01L 21/76838 |
| | | | 257/E21.174 |
| 2005/0233078 A1 | 10/2005 | Boyd et al. | |
| 2006/0070420 A1 | 4/2006 | Quick et al. | |
| 2007/0032862 A1 | 2/2007 | Weber et al. | |
| 2007/0044871 A1 | 3/2007 | Stinson | |
| 2007/0236636 A1* | 10/2007 | Watson | G02B 6/0056 |
| | | | 349/117 |
| 2008/0071347 A1 | 3/2008 | Cambronne | |
| 2009/0126627 A1 | 5/2009 | Quick et al. | |
| 2009/0198314 A1 | 8/2009 | Foster et al. | |
| 2010/0188962 A1* | 7/2010 | Yasuda | G11B 7/13922 |
| | | | 369/112.28 |
| 2010/0279023 A1 | 11/2010 | Kusinski et al. | |
| 2012/0051378 A1* | 3/2012 | Kar | H01L 21/223 |
| | | | 257/77 |
| 2012/0150019 A1* | 6/2012 | Elgort | G01R 33/4828 |
| | | | 600/421 |
| 2012/0296350 A1* | 11/2012 | Kar | A61L 29/106 |
| | | | 606/151 |
| 2013/0197473 A1* | 8/2013 | McMillan | A61B 18/203 |
| | | | 604/501 |
| 2016/0118265 A1* | 4/2016 | Goddard | H01L 21/30604 |
| | | | 438/746 |

OTHER PUBLICATIONS

Ramakrishna, S.A., "Physics of Negative Refractive Index Materials", 2005, Reports on Progress in Physics, 68, p. 449-521. *** See Priority Application U.S. Pat. No. 10,358,723.

Tarr, M., "Conductors and Insulators", 2007, p. 1-7. *** See Priority Application U.S. Pat. No. 10,358,723.

Knovel Critical Tables, 2008, 2nd Ed., p. 1. See Priority Application U.S. Pat. No. 10,358,723.

Helmus, et al. "Biocompatibility: Meeting a Key Functional Requirement of Next-Generation Medical Devices", 2008, Society of Toxicologic Pathology, 36, p. 70-80. *** See Priority Application U.S. Pat. No. 10,358,723.

O'brien, A., "Welding Handbook, vol. 4—Materials and Applications, Part 1", 2011, American Welding Society, 9th Ed., p. 1. *** See Priority Application U.S. Pat. No. 10,358,723.

Accuratus, "Aluminum Oxide, Al2O3 Ceramic Properties", 2013; p. 1-3. *** See Priority Application U.S. Pat. No. 10,358,723.

"Handbook of Reference Data for Nondestructive Testing", 2002, ASTM International, p. 1. *** See Priority Application U.S. Pat. No. 10,358,723.

Byars, H.G., "Corrosion Control in Petroleum Production-Chapter 4-Materials Selection-Metals", 1999, NACE International, p. 69-83. *** See Priority Application U.S. Pat. No. 10,358,723.

UC Davis, "Chemistry of Aluminum", 2015, p. 1-3. *** See Priority Application U.S. Pat. No. 10,358,723.

Schuh, et al., "Mechanical Behavior of Amorphous Alloys", ScienceDirect, Acta Materialia, vol. 55, 2007. pp. 4057-4109. *** See Priority Application U.S. Pat. No. 10,358,723.

Hermawan, et al., "Biomedical Engineering-From Theory to Applications", Chapter 17, "Metals for Biomedical Applications", Prof. Reza Fazel (Ed.), ISBN 978-953-307-637-9, InTech. Aug. 2011, pp. 411-430. *** See Priority Application U.S. Pat. No. 10,358,723.

NACE International, Houston, Texas, http://www.nace.org/CorrosionCentral/Corrosion-1 0 1/Intergranular-Corrosion, "Intergranular Corrosion". *** See Priority Application U.S. Pat. No. 10,358,723.

* cited by examiner

SYSTEM FOR SURFACE MODIFICATION BY LASER DIFFUSION

CROSS REFERENCE TO RELATED APPLICATIONS

This application is a divisional application of U.S. non-provisional patent application Ser. No. 13/969,055 entitled "SYSTEM AND METHOD FOR SURFACE MODIFICATION BY LASER DIFFUSION" filed Aug. 16, 2013, which is herein incorporated by reference in its entirety.

FIELD

Disclosed embodiments relate to laser-based systems for processing of materials to form articles having modified surfaces which provide a modified overall response to incident electromagnetic fields as compared to the bulk of the material.

BACKGROUND

Magnetic Resonance Imaging (MRI) is a medical imaging technique commonly used to image inside the human body. Generally a strong magnetic field (e.g., 1.5 T) is applied to the patient to align the nuclear magnetization vectors of hydrogen atoms in the water of the tissue of the patient under investigation. Simultaneously a RF (e.g., 63.86 MHz) magnetic field (~0.14 µT) is applied to perturb the aligned magnetization, causing the hydrogen nuclei to emit energy signatures that are detectable by a scanner in the MM system.

The MRI signal is used to construct an image. Different tissues are detected because the protons in various tissues return to their equilibrium nuclear magnetization states at different rates. This effect is used to create contrast among different types of tissues. Diseased tissues, such as tumors, can be detected in this manner as well.

A time-varying magnetic field creates an electric field within any electrically conductive material and the electric field, in turn, induces an electric current, referred to as the "eddy current". Generally the electromagnetic field penetrates into metals up to a certain depth, commonly referenced to a "skin depth". An electromagnetic wave entering a conducting surface is damped so that the current density is largest near the surface of the conductor and reduces in amplitude by a factor 1/e at a distance referred to as the skin depth (δ) of the electrical conductor from its surface given by:

$$\delta = [2/(\omega\mu_0\sigma)]^{1/2}$$

where ω is the angular frequency of the radiation, $\mu_0$ is the permeability of the radiation in a vacuum, and σ is the electrical conductivity of the metal. δ can be seen to decrease if the electrical conductivity (σ) increases. For example, at ω=60 Hz in copper, δ is about 8.5 mm. At high frequencies δ may be much smaller (shallower).

The eddy current can heat up the electrically conductive material by the Joule effect and this process is called induction heating. Induction heating can cause thermal damage to tissues while conducting MRI scans for patients wearing implants that have leads, such as in spinal fusion stimulators, cardiac pacemakers and neurostimulation systems. A maximum temperature change of 25.38° C. has been reported for a deep brain stimulation implant shortly after initiating MM. The heating can be more severe at metal tips. A temperature elevation of 63.18° C. has been reported to have occurred at the tip of a pacing electrode (unattached to a cardiac pacing pulse generator) within 90 s of initiating MM.

Although selection of a conventional high electrical conductivity metal material can reduce MRI-induced induction heating somewhat by reducing the amount of energy that is actually introduced into the material via the skin effect, the resulting MRI-induced induction heating may still be too high for certain applications. There is thus a need for new materials and enabling processing systems and methods for forming such materials which provide modified surfaces which generate reduced MRI-induced induction heating.

SUMMARY

This Summary is provided to introduce a brief selection of disclosed concepts in a simplified form that are further described below in the Detailed Description including the drawings provided. This Summary is not intended to limit the claimed subject matter's scope.

One disclosed embodiment comprises a method of forming surface modified substrates including providing a substrate of material (M) having a bulk portion and an outer surface integrated with the bulk portion. A coating including at least one metal X are deposited onto the outer surface. The coating is laser irradiated with a laser beam, wherein atoms of metal X diffuse into the outer surface to form a modified surface layer including both M and atoms of metal X. The bulk portion does not receive the metal X and thus is generally unaffected by disclosed processing remaining as only M. The modified surface layer has a thickness of at least 1 nm, and a 25° C. electrical conductivity that is at least 2.5% above or 2.5% below a 25° C. electrical conductivity of the bulk portion.

Disclosed surface modified substrates are "integrated substrates" such as "integrated articles" which refer herein to structures that have smooth transitions in composition between the bulk portion and its outer surface, that thus lack demarcation therein, such the clear demarcation in the case of an article having an adhesive layer between two layers each having different compositions. In some embodiments, the substrate is in the form of a crystalline lattice, and X is substitutional or interstitial atoms in the lattice of M which can be a metal or a metal alloy. In some embodiments, there is also a thin cladding layer rich in X (>50 atomic %) being primarily X (e.g., 5 nm to 500 nm thick) integrated to and on the modified surface layer comprising M and X, with more M (by atomic %) than X.

The modified surface layer has a thickness of at least 1 nm, typically at least 10 nm, such as 10 nm to 500 nm. The modified surface layer has a 25° C. electrical conductivity which is at least 2.5% above or 2.5% below a 25° C. electrical conductivity in the bulk portion. Embodied as an article, the article can include a frequency selective surface (FSS)-based metamaterial comprising a plurality of modified surface portions, and the plurality of modified surface portions can be arranged to provide a resonant frequency.

Disclosed embodiments also include a system for forming surface modified substrates includes a laser system, and a laser processing chamber. A laser scanner automatically controls a position of the laser beam or an x-y translating stage upon which the laser processing chamber is mounted thereon for scanning the laser beam relative to a substrate of M having a bulk portion and an outer surface integrated with the bulk portion, and a coating including metal organic molecules including at least one metal X or particles of metal X on the outer surface. At laser-heated spots atoms of X from the metal coating diffuse into the outer surface to form a modified surface layer including both M and X. The modified surface layer has a thickness of 1 nm, and a 25° C. electrical conductivity is at least 2.5% above or 2.5% below a 25° C. electrical conductivity in the bulk portion.

BRIEF DESCRIPTION OF THE DRAWINGS

Reference will now be made to the accompanying drawings, which are not necessarily drawn to scale, wherein.

DETAILED DESCRIPTION

Figure 1A:
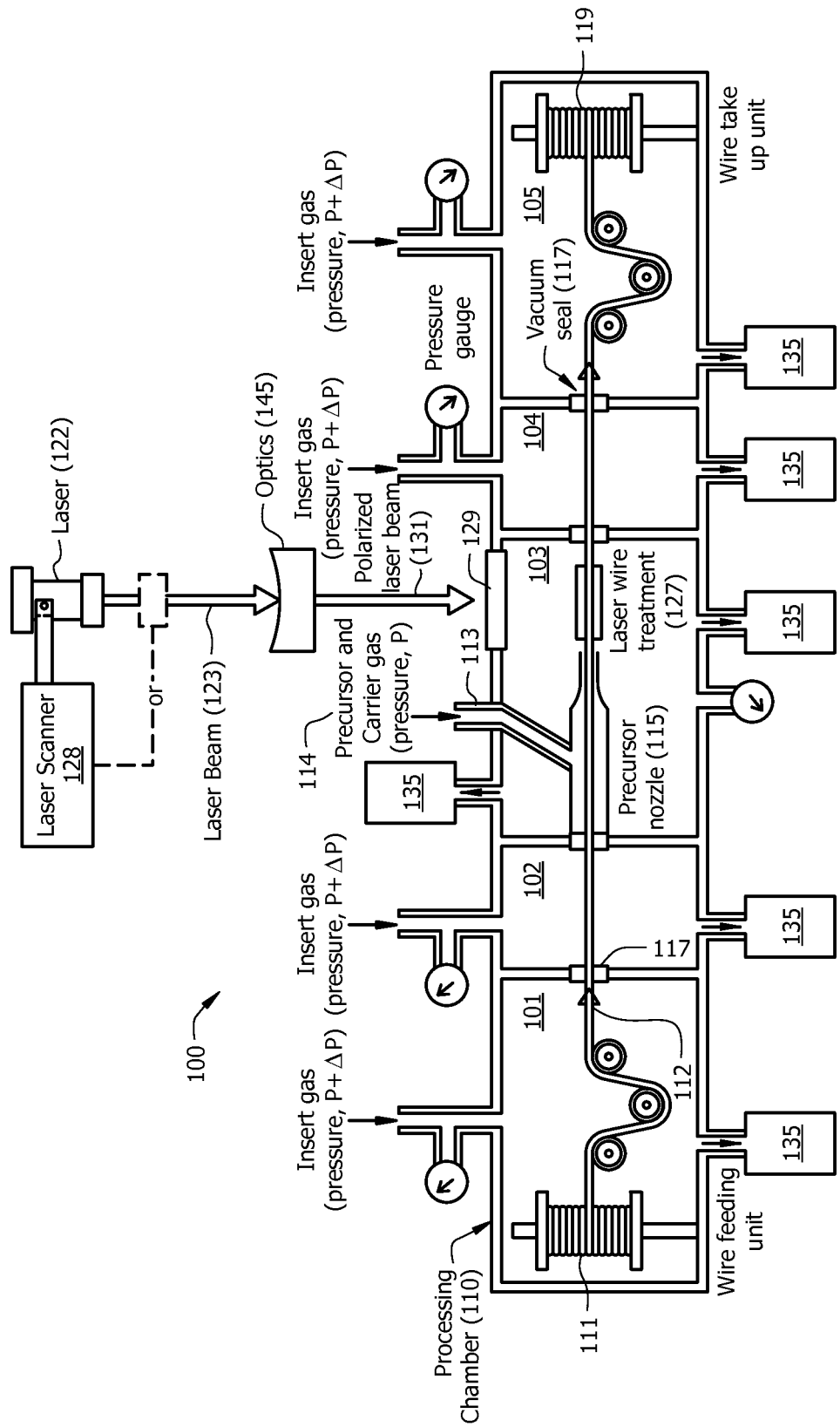
FIG. 1A shows a depiction of an example gas-tight feed through material processing system for laser treatment including laser diffusion for surface modification of wires that includes a sealed chamber comprising five compartments including a laser processing compartment, according to an example embodiment.

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Disclosed embodiments include surface modification of substrates by laser diffusion processing. In one particular disclosed embodiment, the substrate is an article of a medical grade material M modified by modifying the outer surface of M to form a modified surface layer by laser processing that incorporates another material in the outer surface that comprises at least one metal (X). For example, the metal X can comprise one or more of Pt, Pd, Au, Ag or any other noble metal, Cu, Al or any other metal. In the case of two or more different Xs, the another material can comprise a metal alloy. The modified surface layer is at least 1 nm thick, such as from 3 nm to 20 µm, or other thicknesses as prescribed by the skin depth ($\delta$) of the given material for a given application, such as 0.1$\delta$ to 10$\delta$.

The another material can comprise a plurality of particles or an article that can be in the form of a wire, sheet, plate and rod. The incorporation of the metal X in the outer surface of the substrate can be localized to form a patterned modified surface layer, or be global across the outer surface. The processing conditions can be selected so that the modified surface layer of the substrate has 2.5% higher or 2.5% lower 25° C. electrical conductivity as compared to the 25° C. electrical conductivity of M in the bulk portion of the substrate. Disclosed surface modified substrates can be used for leads for medical implants, stents and surgical tools, among other articles and devices.

In one embodiment, the surface modified substrate is a medical component that has a modified surface layer which provides a more electrically resistive surface ($\geq 2.5\%$ higher) than M so that the ability of rapidly varying magnetic fields to create eddy currents in the medical component is reduced, because the electrons are tightly bound to the nuclei in such electrically resistive materials. A "medical component" is defined herein as being formed from a biocompatible material and being part of a medical implant, such as the lead wire of pacemaker, or a medical tool. Medical tools can include needles, knives, tongs, and other items that have the potential for surgical applications in MRI environments. Although M generally comprises a metal or metal alloy, in certain embodiments M may comprise non-metals, such as ceramics or polymer comprising composite materials including an alloy, or a combination of these materials.

When M comprises a metal, M generally comprises a nonmagnetic metal or nonmagnetic metal alloy, such as Ti or Ta in the case of metals, or MP35N, for example, in the case of metal alloys. MP35N (or Co—Cr—Ni—Fe—Mo—Mn alloy) is known as ELGILOY®, from Elgiloy, Ltd. MP35N is nonmagnetic, and possesses a unique combination of ultrahigh tensile strength (up to 300 ksi [=2068 MPa]), good ductility and toughness, and excellent corrosion resistance. MP35N is commonly used for medical lead conductors, such as for cardiac pacemakers. However, M can also be a ceramic, composite or polymeric material, such as plastic wires used for catheters.

M at the outer surface of the substrate can be modified to provide a modified surface layer up to a desired depth, such as on the order of the skin depth, using one or multiple laser beams because of their localized heating capability due to the availability of small spot diameters, such as about 50 µm to 500 µm. A rectangular laser spot of width 50 µm to 500 µm and length 1 mm to 5 mm can be used in one particular embodiment. Lasers allow precise control in delivering energy (by controlling the intensity) to a substrate, and therefore a small thickness beneath the surface of the substrate can be heated with laser(s) without significantly heating the bulk portion of the substrate. The substrate can be laser irradiated with either focused (generally smaller spot sizes) or unfocused laser beams (generally larger spot sizes).

For disclosed chemical decomposition-based processing, metal precursors are used, which are generally metal organic compounds including the metal X, that using precursor vapor deposition can incorporate X into M to form modified surface layers as described herein. Metal organic compound precursors are a class of chemical compounds which include both metals and organic ligands. After deposition in a precursor form, the metal organic molecules can be chemically decomposed at laser-heated spots due to pyrolytic decomposition or photolytic decomposition, or a combination thereof, to form atoms of metal X. In other disclosed embodiments, instead of precursor vapor deposition followed by chemical decomposition processing, a coating of the metal X can be deposited on the surface of the substrate M using a variety of precursors such as the solid, liquid, vapor/gas and plasma phases of the metal X and employing a variety of techniques such as sputtering, electroplating, pulsed laser deposition and wet dipping chemical process, and the coating can contain nanoparticles or micrometer size particles of metal X, or a combination thereof. Some or all of the X atoms can be subsequently diffused by laser heating into the outer surface of the substrate to form a modified outer surface having M and X, such as to increase or decrease the reflectivity of the outer surface to incident magnetic field of interest for MRI applications.

For example, in a particular precursor vapor deposition followed by decomposition process embodiment for surface modifying an outer surface of a substrate with the metal X being Pt, an example commercially available precursor material used is platinum(II) acetylacetonate [$Pt(C_5H_7O_2)_2$] which is not highly sensitive to air or moisture, which can be thermally decomposed at a relatively low temperature (210 to 240° C.). The platinum acetylacetonate molecules decompose into Pt atoms and volatile acetylaceton molecules as shown below:

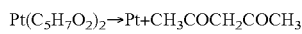

$$Pt(C_5H_7O_2)_2 \rightarrow Pt+CH_3COCH_2COCH_3$$

The Pt atoms generated by the decomposition on the outer surface of the substrate subsequently diffuse into the laser-heated substrate locations.

X is typically in a range of 0.05 to 10 weight % of the modified surface layer. Since the substrate workpiece (particles or an article) can be locally heated to very high temperatures (close to its melting temperature) with laser(s) in a controlled manner, the diffusion coefficient of the solute atoms being the metal X has been unexpectedly found to be up to about five orders of magnitude higher than that obtained under thermal equilibrium heating conditions. As defined herein "thermal equilibrium heating conditions" refer to the situation where the entire substrate workpiece is at the same temperature and the temperature does not vary spatially within the workpiece with time. Disclosed laser surface diffusion processes thus enable introducing far more atoms of X into M than what can be achieved in conventional equilibrium heating processes, including more X atoms per unit volume, and in some cases a deeper diffusion depth. Also rapid heating to high temperatures followed by fast cooling inherent in laser processing enhances the solid solubility, resulting in higher concentration of X in M than what is prescribed by their equilibrium phase diagram. Accordingly, the reflectivity of M with added X can be correspondingly increased more by disclosed laser diffusion processes as compared to conventional equilibrium heating processes.

Laser polarization is another parameter that can be used to enhance the diffusivity of the metal X in M. The polarization described herein represents the line or curve traced by the tip of the electric field vector of the radiation from a laser on a plane perpendicular to the direction of propagation of the radiation. The diffusivity of X depends on the vibrational frequencies of the M atoms. In conventional heating and even in unpolarized laser heating, the atoms vibrate randomly resulting in phonons with randomly varying energy. Also the phonons propagate inside the material incoherently and in random directions. These randomly moving incoherent phonons in M can impede the migration of X from one point to another point in M and, therefore, reduce the diffusivity of X. In this embodiment, polarization can be used to control the direction of motion of the phonons in M and, thereby, affect the diffusivity of X in M, generally to increase the diffusivity of X in M.

The polarized laser beam can be linear, circular or elliptical, or a combination thereof. Generally the beam emitted from a laser system is unpolarized. Polarized beams can be formed from the unpolarized beam using one or more polarizers placed in the system 100 in FIG. 1A and system 150 in FIG. 1B described below shown as optics 145, such as based on birefringent materials including a Wollastom prism, Rochon prism Sénarmont prism, or using other anisotropic material-based optical elements such as a Pockels cell. Depending on the microstructural properties of M such as the grain size, crystal structure, lattice parameters and preferred orientation of the crystalline planes, and the properties of X such as the electrochemical, thermomechanical, electromagnetic and physical properties, the diffusivity of X can be enhanced by selecting an appropriate non-random polarization.

Disclosed embodiments also include new material processing systems which provide laser treatment for substrates such as particles or wire materials comprising a metal (or metal alloy) substrate material M having a bulk portion and an outer surface. The processing provided modifies the outer surface of the substrate by forming a modified surface layer modified by adding another material(s) X relative to the M over at least a portion of the outer surface.

FIG. 1A shows a depiction of an example gas tight feed through material processing system 100 for laser treatment of substrates shown as a metal (or metal alloy) wire 112 that includes a processing chamber 110 comprising five sealed compartments 101-105 having vacuum seals 117 between the respective compartments. Since the process implemented by processing system 100 can utilize a metal organic compound as a precursor that may be toxic and/or pyrophoric, the processing chamber 110 of processing system 100 being has a sealed chamber (comprising sealed compartments 101-105) allows disclosed laser diffusion to be carried out safely. Vacuum pumps 135 are provided to provide the exhaust flows shown out from the various compartments 101-105.

A wire feeding spool 111 is in compartment 101 and the wire 112 shown is collected with a take up spool 119 in compartment 105 after the wire 112 passes through two inert or unreactive gas-filled buffer compartments 102 and 104, and the laser processing compartment 103. The wire 112 comprises material M which has a bulk portion and an outer surface, which generally receives processing before being placed in compartment 101 to remove surface impurities, such as removal of thin metal oxide layers when M is a metal or metal alloy.

The wire 112 (or other substrate being processed) may comprise a single material M, or have an outer surface cladding comprising M over a bulk portion being another material. Laser processing described below can be subsequent to wire extrusion, where the wire has been co-extruded from at least two materials, such as a substrate cladding comprising M over and integral to a support comprising another material. In laser processing compartment 103, the metal(s) X precursor gas or vapor including the metal(s) X together with a carrier gas (e.g., argon) 114 is delivered via an inlet 113 to a precursor nozzle 115. To provide the precursor gas, a precursor solution can be evaporated using a hot plate, such as maintained at 130° C., assisted by a bubbler (e.g., Ar bubbler). Metallorganic compounds are generally toxic and pyrophoric. The laser processing compartment 103 allows containing both the pre-processed and post-processed substrate under inert or reactive conditions, and thus enables isolating M from ambient air completely. Processing system 100 also enables batch or continuous processing of substrates such as wire 112 or particles.

The modified surface layer is formed in laser processing compartment 103. In some embodiments, there is also a thin cladding layer of primarily atoms of X (defined as >50% of the atoms), being e.g., 5 nm to 500 nm thick, formed on top of the modified surface layer. One or both the laser irradiating and/or the partial pressure of the precursor gas may be used as variables to control whether or not a thin cladding layer of primarily X (by atomic %) is formed on top of the modified surface layer, and its thickness. For example, lower partial pressures of the metal(s) X precursor gas, such as about ≤100 mTorr, may only form the modified surface layer, while higher partial pressures of the metal(s) X including precursor gas, such as about 500 mTorr, or more, may be used to also form the thin cladding layer of primarily atoms of X on and integrated with the modified surface layer. For example, the thin cladding layer of primarily atoms of X can include 80 to 100 atomic % X (with the balance, if any, being M), while the modified surface layer can include 5 to 10 atomic % X, with the remainder being M.

The vacuum pumps 135 generally provide at least a rough vacuum (e.g., ≤about 1 mTorr) in compartments 101-105 when no precursor or carrier gas is flowing. With metal organic precursor gas or vapor together with carrier gas 114 flowing the pressures in compartments 101-105 can be kept at around 0.1 to 1 atmosphere (atm). During operation, compartments 101-105 can be maintained at a slightly higher pressure (e.g., 1.05 atm) as compared to the pressure (e.g. 1 atm) in the laser processing compartment 103. The buffer compartments 102 and 104 enable holding and removing any metal organic precursor gas or vapor and any chemical reaction products that might otherwise leak into compartments 102 and 104 from laser processing compartment 103.

The carrier gas can be an inert or non-reactive gas (e.g., argon or nitrogen), or a reactive gas that enhances the chemical decomposition of the metal organic precursor molecules at the surface of the wire 112, or a combination thereof. The metal organic precursor flow rate and the precursor nozzle 115 can be designed to improve the adsorption of the precursor molecules on the outer surface of the wire 112, and the remaining metal organic precursor molecules can exit the precursor nozzle 115 with appropriate velocity and flow direction to create a precursor shroud around the wire 112 in the laser-wire interaction (laser wire treatment) zone 127.

Processing system 100 is also shown including optics 145 which processes the laser beam 123 to provide the polarized laser beam 131 shown. Optics 145 can receive an unpolarized (or randomly polarized) laser beam 123 from laser system 122 (including a laser driver) of a Gaussian irradiance distribution and transform it into a polarized laser beam 131 of uniform or any other irradiance distribution and simultaneously focus the beam. The polarized laser beam 131 can have linear, circular, or azimuthal polarization, or any other polarization depending on the design of the optics 145.

System 100 also includes a laser scanner 128 which is a computer controlled device that automatically controls the position of the laser beam 123 to produce desired patterns (e.g., such as to form the frequency selective surface (FSS) described below). Laser scanner 128 can comprise an acousto-optic device (e.g., Acousto-Optical Tunable Filter (AOTF) or AO deflector) electronic scanning system. Alternatively, the laser beam position may be fixed, and a mechanical system (e.g., x-y translation stage, see FIG. 1B described below) may be used to move the processing chamber. Laser processing compartment 103 includes an optically transparent window 129 for transmitting the polarized laser beam 131 to allow laser processing in laser processing compartment 103. The adsorbed metal organic precursor molecules decompose due to chemical reactions at the laser-heated surface of the wire 112 in the laser wire treatment zone 127, and atoms of the metal X and other reaction products are produced. As the reaction products move away from the laser wire treatment zone 127, the precursor shroud shown as nozzle 115 supplies the metal organic precursor molecules to the surface of the wire 112 to continue the chemical reactions for producing the atoms of metal X continuously. At least a portion of the atoms of X subsequently diffuse into the outer surface of the wire 112.

Thermal stresses might develop in the wire 112 due to laser heating in the laser wire treatment zone 127. These stresses can be relieved by heating the wire in the buffer compartment 104 after the laser wire treatment zone 127, using one or more laser beams of appropriate irradiance profiles. Also the development of these stresses can be prevented by pre-heating the wire in the buffer compartment 102 or in the laser processing compartment 103 before laser treatment zone 127 or in both the compartments, using one or more laser beams of appropriate irradiance profiles. To remove the reaction products and any residual precursor molecules from laser processing compartment 103, a steady flow pattern can be established using one or more inlet ports to deliver inert gases to the laser processing compartment 103 and using one or more exhaust ports coupled to a vacuum pump 135 to expel the gas mixture. This process can enable maintaining a steady pressure in laser processing compartment 103 during processing. Similarly, as noted above, the other compartments 101, 102, 104 and 105 are generally equipped with exhausts coupled to a vacuum pump to release excess gases in order to maintain steady pressures.

Optics 145 provides the functions of polarization, non-uniform (Gaussian) to more uniform intensity distribution, and focusing, referred to herein as "beam shaping optics". Optics 145 can receive the unpolarized (or randomly polarized) laser beam 123 of Gaussian irradiance distribution and transform it into a polarized laser beam 131 of uniform or any other irradiance distribution and simultaneously focus the beam. As noted above, the transformed laser beam can have linear, circular, azimuthal or any other polarization depending on the design of the optics 145.

Although processing system 100 shown in FIG. 1A is described for precursor vapor deposition followed by chemical decomposition processing, as described above instead of precursor vapor deposition followed by chemical decomposition processing, in an alternate embodiment a coating of the metal X can instead be deposited on the substrate by other techniques such as sputtering, electroplating or a wet dipping chemical process. The coating can contain nanoparticles or micrometer size particles of X, or a combination thereof. In this alternate embodiment, the processing system excludes the X precursor gas or vapor including the metal(s) X, but can include a carrier gas 114, an inlet 113 and a nozzle 115 which can be used as the carrier gas nozzle.

In this alternate embodiment a metal coating can be deposited before the wire 112 (or other substrate being processed) enters the processing system 100, i.e., the wire feeding spool 111 can contain metal-coated wire. On the other hand, the metal coating need not be deposited before the wire 112 (or other substrate being processed) enters the processing system 100, i.e., the wire feeding spool 111 can contain just an uncoated wire (substrate M), and in that case the compartment 102 will house a coating deposition system, such as a sputtering, electroplating or wet dipping chemical processing system.

A vacuum is still generally included in this alternate embodiment because air is removed from the processing system first and then back filled with an inert gas (e.g., argon). Although a vacuum is generally used to eliminate the reaction products when the X precursor gas or vapor is used in processing systems such as processing system 100 in FIG. 1A, a vacuum (i.e., pressure differential in various compartments) is not necessary for this alternate embodiment. However the coating deposition system, such as a sputtering, electroplating or wet dipping chemical processing system, may include a vacuum for depositing a coating of X on M. For example, the wire 112 (or other substrate being laser processed) can be cleaned by removing the oxide scale from the substrate surface using a sputtering technique or a laser ablation method and in that case, a vacuum would be used to remove the sputtered or ablated products. This cleaning process can be carried in compartment 102. So compartment 102 can house two systems, a cleaning system and a coating system.

Figure 1B:
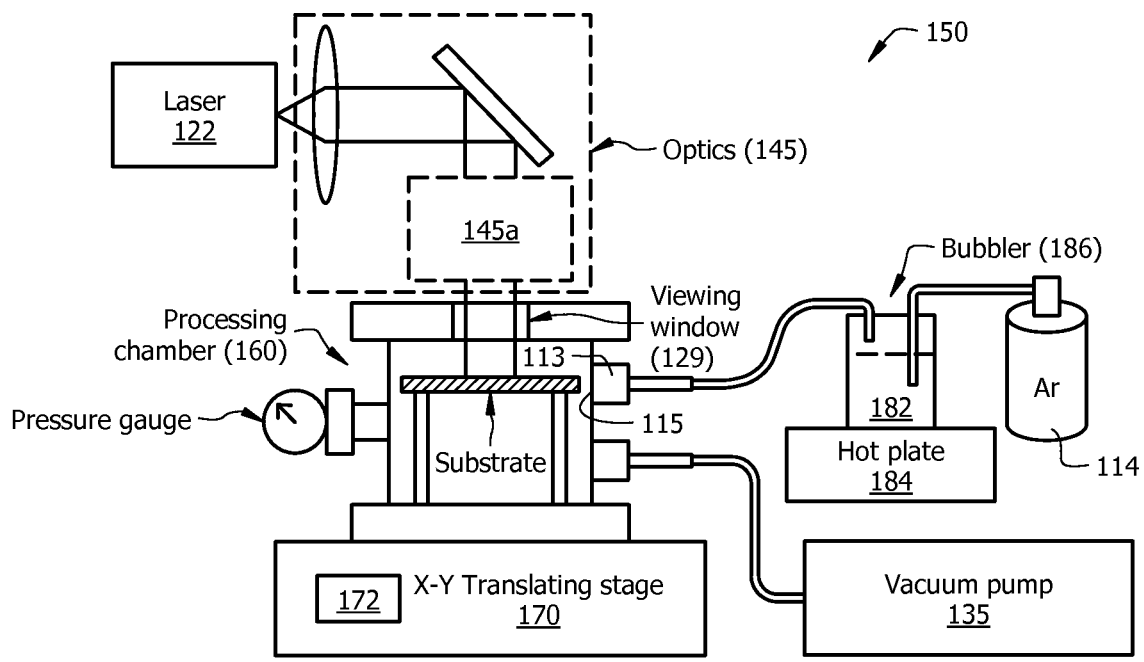
FIG. 1B shows a depiction of another example gas-tight feed through material processing system for laser treatment including laser diffusion for surface modification of metal wires that includes a single sealed processing chamber, according to an example embodiment.

In another alternate embodiment, the processing chamber is moved by an X-Y translation stage which can remove the need for laser scanner 128 as well as structures for moving the wire 111 through the chambers 101-105 shown in FIG. 1A as 111 (wire feeding spool) and 119 (take up spool). FIG. 1B shows a depiction of another example gas-tight feed through material processing system 150 for laser treatment including laser diffusion for surface modification of substrates which includes a single sealed processing chamber 160, according to an example embodiment. Processing system 150 includes a precursor solution in container 182, and a carrier gas 114 shown as Ar that bubbles though the container 182 to the inlet 113 and nozzle 115 for injecting the precursor gas and carrier gas into processing chamber 160. The precursor solution in container 182 is thus evaporated using the hot plate 184 such as maintained at 130° C., assisted by the bubbler 186 shown. The X-Y stage 170 is generally computer position controlled by position controller 172 which translates the processing chamber 160 based on a predetermined spatial pattern. Polarizing and beam shaping optics depicted in FIG. 1B as 145a generally include a polarizer and beam shaping lens (BSL).

Figures 2A, 2B:
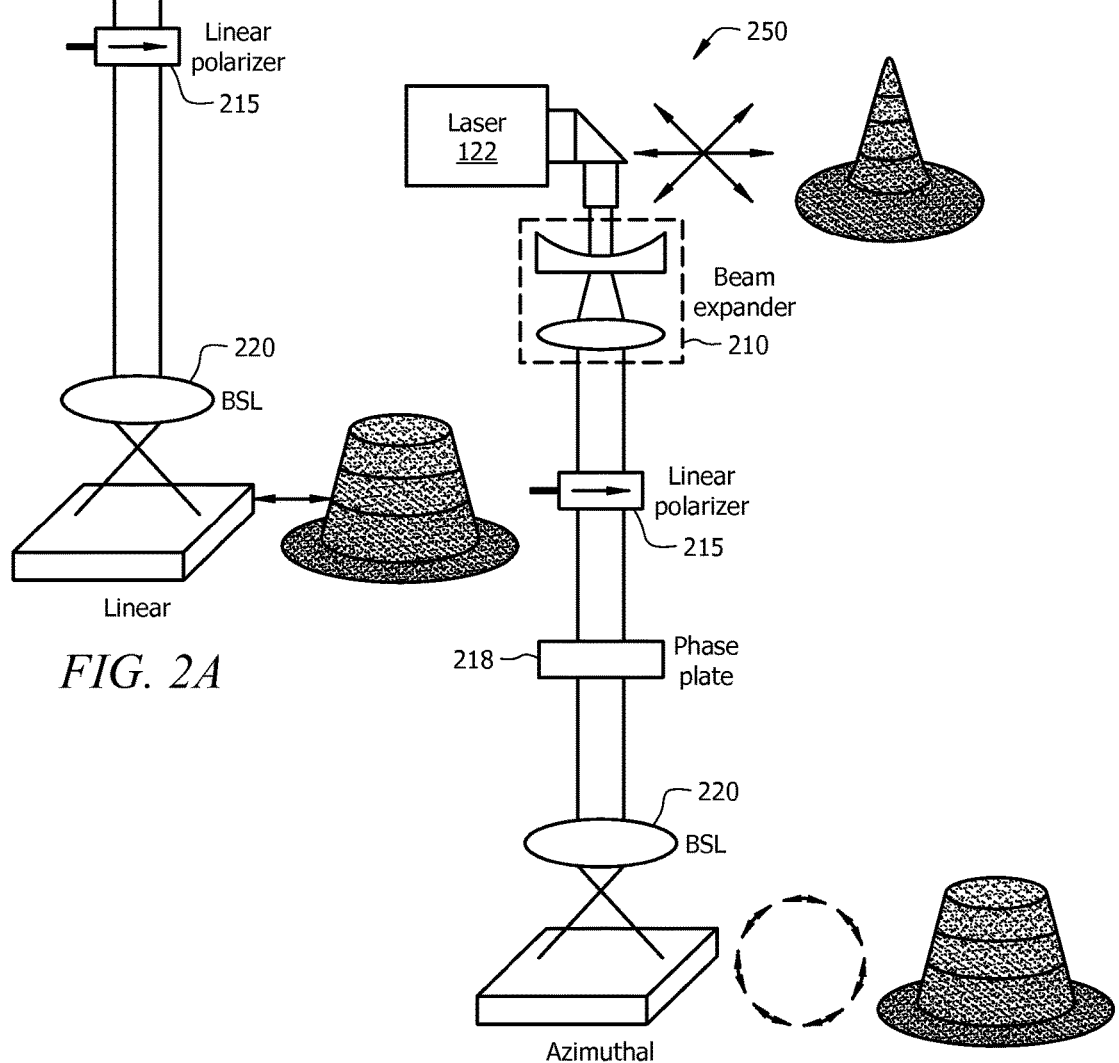
FIGS. 2A and 2B each depict optical arrangements for polarizing and beam shaping of laser beams that can be used to generate polarized flat-top beams.

FIGS. 2A and 2B depict example optical arrangements for polarizing and beam shaping that can be used to generate polarized flat-top beams. Conventional Gaussian laser beams have high power density (W/m$^2$) at the center of the beam and then the power density decreases rapidly toward the edge of the beam, and consequently the Gaussian beams will heat up the moving wire non-uniformly with a much higher temperature near the laser beam center than elsewhere of the laser-heated region. Flat-top laser beams, on the other hand, have uniform power density, and consequently allow uniform heating over a wide region of the moving wire, resulting in uniform diffusion of X into M. A beam shaping lens (BSL) as used herein refers to a lens that transforms a Gaussian laser beam into a flat-top laser beam, such as a plano-convex lenses. The BSL is a special lens that diffracts the Gaussian laser beam in such a way that the wavelets of non-uniform power density interfere to generate a wavefront of uniform power density. The lens is generally designed by varying the radius of curvature of the lens surface as a function of the radius of the lens. The BSL can also be designed by varying the refractive index of the lens material as a function of the radius of the lens. The refractive index is varied by varying the concentrations of various constituents of the lens material. Another method for designing BSL is to deposit a coating on the lens surface with varying thickness of the coating or varying refractive index of the coating or a combination thereof.

FIG. 2A shows a first optical arrangement 200 for polarizing and beam shaping to produce a linearly polarized flat top beam from an unpolarized Gaussian beam, where the unpolarized Gaussian beam output from the laser in laser system 122 is processed by a beam expander 210, polarized by a linear polarizer 215, and is then shaped by a BSL 220. FIG. 2B shows a second optical arrangement 250 for polarizing and beam shaping to produce an azimuthally polarized flat top beam from an unpolarized Gaussian beam, where the unpolarized Gaussian beam output from the laser in laser system 122 is processed by a beam expander 210, polarized by a linear polarizer 215, is processed by a phase plate (e.g., quarter wave plate) 218, then by a BSL 220.

Figure 3:
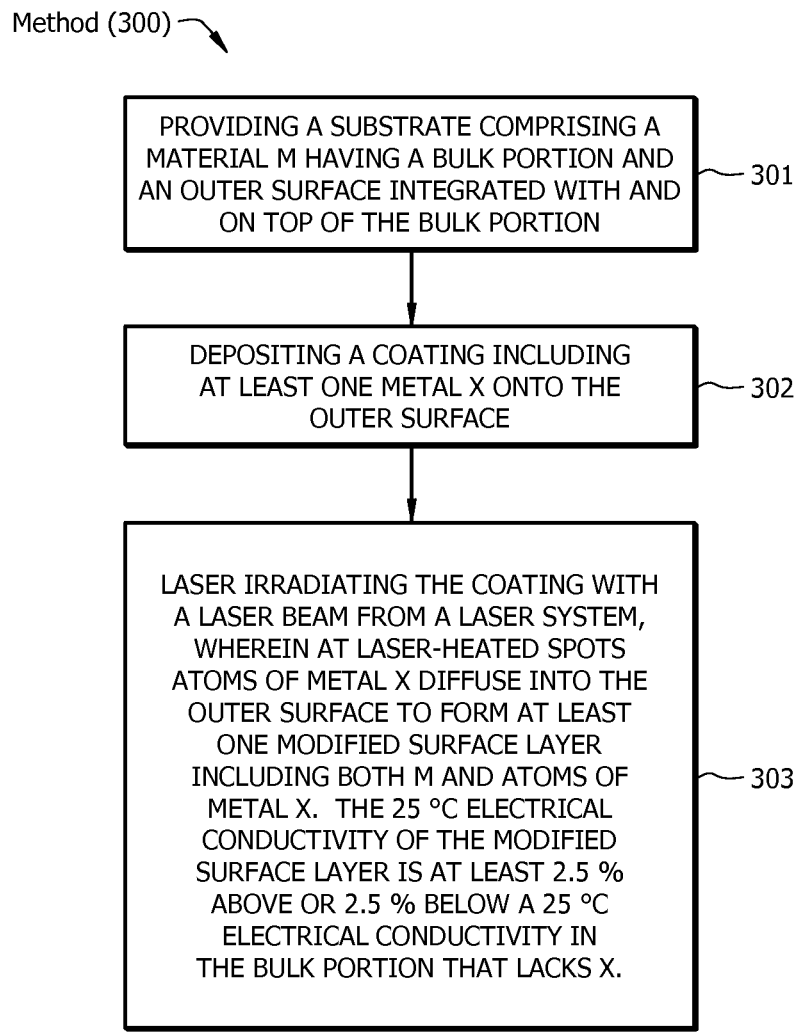
FIG. 3 is a flow chart that shows steps in an example method for forming surface modified articles, according to an example embodiment.

FIG. 3 is a flow chart that shows steps in an example method 300 for forming surface modified substrates, according to an example embodiment. Step 301 comprises providing a substrate comprising M having a bulk portion and an outer surface integrated with and on top of the bulk portion. Step 302 comprises depositing a coating including at least one metal X onto the outer surface of M. The depositing can comprise vapor depositing metal organic precursor molecules including metal X or depositing a coating of metal X containing nanoparticles or micrometer size particles of metal X by a technique such as sputtering, electroplating or wet dipping chemical.

Step 303 comprises laser irradiating the coating of metal organic molecules or coating of metal X with a laser beam from a laser system, wherein atoms of metal X diffuse into the outer surface of M to form at least one modified surface layer including both M and atoms of metal X. In the case the coating is of metal organic molecules, the metal organic molecules decompose chemically at laser-heated spots to form atoms of metal X. In the case of the coating is of X particles, X atoms from the X particles diffuse into the outer surface of M. The modified surface layer generally has a thickness of at least 1 nm, such as >3 nm, such as from 3 nm to 20 μm, or other thickness as prescribed by the skin depth of a given material, and a 25° C. electrical conductivity of the modified surface layer is at least 2.5% above or at least 2.5% below a 25° C. electrical conductivity in the bulk portion that lacks X.

EXAMPLES

Disclosed embodiments are further illustrated by the following specific Examples, which should not be construed as limiting the scope or content of this Disclosure in any way.

In one example embodiment a BSL was designed for transforming an unpolarized Gaussian laser beam from a laser source to a flat-top laser beam for laser diffusion processing. Metal organic precursor molecules on a Ti or Ta (substrate) sheet were irradiated with a laser beam from a laser system analogous to system 100 shown in FIG. 1A to incorporate Pt atoms into the Ti and Ta sheets. Transmitted magnetic field strengths at 63.86 MHz were measured to determine the transmittance of the surface modified sheets. The treated Ti sheets had lower transmittance than the as-received Ti samples due to increased electrical conductivity. The treated Ta sheets, on the other hand, had higher transmittance than the as-received Ta samples due to reduced electrical conductivity. The increased electrical conductivity may be due to the diffused Pt atoms and the decreased electrical conductivity may be due to increased oxygen atoms.

Regarding the polarization effect, the samples irradiated by a linearly polarized laser beam had higher Pt concentration and exhibited more changes in the transmittance at 63.86 MHz than the samples prepared by irradiating with laser beams of other polarizations such as circularly or randomly polarized laser beams. In another example embodiment transmission measurements were carried out and a mathematical model presented to determine the electromagnetic properties of disclosed surface modified metals. Particularly the reflectivity of metals for just magnetic fields that vary with time at moderate frequencies, such as 30 to 100 MHz, was investigated. Since commercial instruments are not readily available for such frequency ranges, the inverse problem approach of this study provided a good alternative. Ti sheets of thicknesses 25 μm and 50 μm were considered as control test samples, and Pt was diffused into some of the Ti sheets by laser irradiating metal organic molecules including Pt on the sheet to understand how the properties of metals can be modified at the low frequency of interest.

The refraction and absorption indices of Ti were determined for a magnetic field of frequency 63.86 MHz. Other electromagnetic properties of Ti such as the relative permittivity, conductivity, absorption coefficient and reflectivity were also calculated. The electrical conductivities of the disclosed platinumized surfaced Ti sheet and the as-received Ti sheets were found to be $2.30 \times 10^6$ and $2.51 \times 10^6$ $m^{-1}\Omega^{-1}$, respectively, which is an increase by 9.1%, and, consequently, the reflectivity of the former was higher than the reflectivity of the latter. This increment in electrical conductivity is believed to be due to the added Pt in Ti increasing the free electron density in Ti. Additionally, the absorbance of the platinumized surfaced Ti sheet at a magnetic field of frequency 63.86 MHz decreased by 0.9% when compared to that of the as-received Ti sheet, indicating that the substrate would be heated less by the time-varying magnetic field.

In another example embodiment thin sheets of Ti and Ta were heated with laser beams of different polarizations to diffuse Pt from a platinum precursor into the sheets without melting the sheets. The reflectivities of the sheets were measured for four polarizations of a Nd:YAG laser (free space wavelength of 1064 nm) and compared with theoretical results. When the surface roughness was small compared to the laser wavelength, the surface can be considered smooth for which the measured reflectivity is almost equal to the Fresnel reflectivity. On the other hand, when the surface roughness is comparable to the laser wavelength, the effects of surface asperity dominate and the reflectivity is significantly lower than the Fresnel reflectivity. The reflectivities are almost the same for the four polarizations at normal incidence, while the reflectivity for p-polarization embodiment is lower than the other three polarizations at the incident angle of 45°. For the same polarization, however, the reflectivity at oblique incidence is higher than at the normal incidence due to the smaller effective roughness of the surface.

Based on the measured reflectivity of the Ti and Ta sheets, the substrate surface temperature was estimated during laser irradiation to analyze the Pt content in the disclosed laser-treated samples. The concentrations of C and O impurities and laser-diffused Pt atoms in the Ti and Ta samples were measured using Energy-dispersive spectroscopy (EDS). Higher concentrations of Pt atoms were observed in the samples that were laser-treated at lower scanning speeds. This result may be due to higher surface temperatures produced at lower scanning speeds for the same irradiance of the laser beam. Slightly higher Pt concentration was obtained with linear polarization than with azimuthal polarization, because of lower reflectivity and, consequently, higher surface temperature in the former case. Also the linearly polarized laser beams may facilitate the migration of Pt atoms in the substrate by affecting the phonons differently compared to the azimuthally polarized laser beams.

In another example embodiment platinum from a platinum precursor was diffused into Ti and Ta sheets using a Nd:YAG laser. The polarization of the laser was modified to produce linearly or azimuthally polarized beams to carry out laser diffusion experiments. The effect of impurities on the transmission of a magnetic field oscillating at the frequency 63.86 MHz was examined. Pt was found to decrease the transmittance of Ti and oxygen increase the transmittance of Ta compared to that of the as-received Ti and Ta sheets.

For disclosed laser-treated Ti samples, the reduction in the transmittance at a magnetic field at 63.86 MHz may be attributed to increased DC electrical conductivity due to two effects. Since the electrical conductivity of Pt is significantly higher than that of Ti, the diffused Pt atoms reduce the transmittance of the Ti sheets by increasing the electrical conductivity of the surface modified sheets. The second effect arises from the laser polarization. Linearly polarized lasers can restrict the lattice oscillation to certain directions and excite the local vibration modes of Pt and Ti atoms to increase the diffusion of Pt into the Ti sheets with the consequence of higher conductivity and lower magnetic field at 63.86 MHz transmittance.

For disclosed laser-treated Ta samples, the diffused Pt atoms did not increase the electrical conductivity of Ta as much as in the case of Ti because the electrical conductivities of Pt and Ta are almost the same. However the transmittance of the treated samples increased compared to the as-received control sample, which may be attributed to increased oxygen concentration in the samples. The presence of oxygen can form $TaO_2$, inducing dielectric properties in the samples. This transformation raises the transmittance of the Ta samples since the magnetic field can propagate through the samples without being absorbed.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention claimed is:

1. A system for forming a surface modified substrate, the system comprising:
   at least one laser source configured to generate a Gaussian laser beam;
   a translation stage;
   a controller coupled to the translation stage;
   a single sealed laser processing chamber mounted onto the translation stage and including
     a substrate receiving support,
     an optical window for transmitting the Gaussian laser beam to the substrate receiving support, and
     an inlet for receiving a precursor gas comprising metal organic molecules including at least one metal;
   at least one vacuum pump coupled to the single sealed laser processing chamber, the single sealed laser processing chamber being vacuum sealed;
   the controller configured to cause the translation stage to control a position of the Gaussian laser beam for scanning the Gaussian laser beam relative to a substrate of material via two dimensional movement and in a predetermined spatial pattern, the predetermined spatial pattern comprising a frequency selective surface (FSS) pattern, the substrate having a bulk portion, an outer surface integrated with the bulk portion, and a coating including the metal organic molecules including the at least one metal on the outer surface, the metal organic molecules being deposited on the outer surface from the precursor gas;
   the at least one laser source configured to
     decompose the metal organic molecules at laser-heated spots to form the at least one metal, and
     diffuse the at least one metal into the substrate with a diffusivity of X based upon a non-random polarization the at least one laser source;
   a beam expander coupled between the at least one laser source and the optical window;
   a linear polarizer coupled downstream from the beam expander;
   a phase plate coupled downstream from the linear polarizer; and
   a beam shaping lens coupled downstream from the phase plate and configured to transform the Gaussian laser beam into a linearly polarized flat-top laser beam;
   wherein the laser-heated spots atoms of the at least one metal diffuse into the outer surface to form at least one modified surface layer including the bulk portion and the at least one metal;
   wherein the at least one modified surface layer has a thickness of at least 1 nm; and
   wherein a 25° C. electrical conductivity of the at least one modified surface layer is at least 2.5% above or 2.5% below a 25° C. electrical conductivity in the bulk portion.

2. The system of claim 1, further comprising:
   a store of a carrier gas;
   a bubbler coupled to the store of the carrier gas and to combine a precursor solution and the carrier gas;
   a hot plate coupled to the bubbler and configured to boil the precursor solution with the carrier gas in the bubbler to generate a precursor gas combined with the carrier gas; and
   a conduit configured deliver the precursor gas combined with the carrier gas to the single sealed laser processing chamber.

3. The system of claim 1 wherein the at least one vacuum pump is configured to place the single sealed laser processing chamber in a rough vacuum state when the precursor gas is not flowing, and place the single sealed laser processing chamber in pressurized state with a pressure range of 0.1-1 atmospheres when the precursor gas is flowing.

* * * * *